US011656218B2

(12) United States Patent
Aoki et al.

(10) Patent No.: US 11,656,218 B2
(45) Date of Patent: May 23, 2023

(54) LIQUID TANK FORMATION METHOD, MEASUREMENT DEVICE, AND ANALYSIS DEVICE

(71) Applicant: HITACHI, LTD., Tokyo (JP)

(72) Inventors: Mayu Aoki, Tokyo (JP); Itaru Yanagi, Tokyo (JP); Kunio Harada, Tokyo (JP); Kenichi Takeda, Tokyo (JP)

(73) Assignee: HITACHI, LTD., Tokyo (JP)

(*) Notice: Subject to any disclaimer, the term of this patent is extended or adjusted under 35 U.S.C. 154(b) by 960 days.

(21) Appl. No.: 16/464,835

(22) PCT Filed: Oct. 12, 2017

(86) PCT No.: PCT/JP2017/036944
§ 371 (c)(1),
(2) Date: May 29, 2019

(87) PCT Pub. No.: WO2018/105229
PCT Pub. Date: Jun. 14, 2018

(65) Prior Publication Data
US 2019/0293625 A1 Sep. 26, 2019

(30) Foreign Application Priority Data

Dec. 7, 2016 (JP) .............................. JP2016-237960

(51) Int. Cl.
*G01N 33/487* (2006.01)
*G01N 27/447* (2006.01)
(Continued)

(52) U.S. Cl.
CPC ....... *G01N 33/48721* (2013.01); *G01N 27/00* (2013.01); *G01N 27/04* (2013.01); *G01N 27/44791* (2013.01)

(58) Field of Classification Search
CPC .. G01N 27/00; G01N 27/04; G01N 27/44756; G01N 27/44791;
(Continued)

(56) References Cited

U.S. PATENT DOCUMENTS

2013/0180867 A1\* 7/2013 Rosenstein ...... G01N 27/44713
205/794.5
2014/0158540 A1\* 6/2014 Ohura .............. G01N 27/44791
204/627
(Continued)

FOREIGN PATENT DOCUMENTS

JP 2012-026986 A 2/2012
WO 2015/097765 A1 7/2015

OTHER PUBLICATIONS

Itaru et al., Lab Chip, 2016, 3340-3350 (Year: 2016).\*
International Search Report of PCT/JP2017/036944 dated Nov. 28, 2017.

*Primary Examiner* — Gurpreet Kaur
(74) *Attorney, Agent, or Firm* — Mattingly & Malur, PC

(57) ABSTRACT

A method includes a step of introducing a solution between a substrate with a membrane in which the membrane is provided so as to close an opening and a substrate provided with an independent electrode in which the independent electrode is provided, a step of pressure bonding the substrate with the membrane and the substrate with the independent electrode through a partition wall, and a step of forming a sealed liquid tank surrounded by at least the membrane and the partition wall by the pressure bonding, and arraying of a solid-state type nanopore sequencer is simply performed.

2 Claims, 20 Drawing Sheets

(51) Int. Cl.
  *G01N 27/04* (2006.01)
  *G01N 27/00* (2006.01)
(58) Field of Classification Search
  CPC ......... G01N 27/4473; G01N 27/48707; G01N 27/48735; G01N 33/48721; G01N 33/48728; C12Q 2565/631; C12Q 1/6813; C12Q 1/6876; C12Q 1/6825; C12Q 1/6869; C12Q 1/68; C12Q 2563/116; B81B 1/00
  See application file for complete search history.

(56) References Cited

U.S. PATENT DOCUMENTS

| | | | |
|---|---|---|---|
| 2016/0327513 A1 | 11/2016 | Yanagi et al. | |
| 2017/0363609 A1* | 12/2017 | Tabard-Cossa | ............................ G01N 33/48721 |
| 2020/0332434 A1* | 10/2020 | Yanagi | ....................... C25F 3/14 |

* cited by examiner

LIQUID TANK FORMATION METHOD, MEASUREMENT DEVICE, AND ANALYSIS DEVICE

TECHNICAL FIELD

The present invention relates to a method of forming a liquid tank, a measurement device and an analysis device.

BACKGROUND ART

As a biological sample analyzer for analyzing biological samples such as DNA and proteins, development of a blockage current method nanopore sequencer has been advanced. The blockage current method nanopore sequencer is configured by a membrane of a thin film having a pore of the same size as that of a biological sample, and a liquid tank having electrodes disposed above and below the membrane. In such a configuration, the liquid tank is filled with a solution, and the biological sample is introduced to one side of the liquid tank. A voltage is applied to the electrodes, and a change in a value of the current flowing between the two electrodes is measured when the biological sample passes through the pore. With the measurement described above, structural features of the biological sample are determined.

There is a solid-state type as the present method of forming a nanopore sequencer of the blockage current method. The solid-state type is a method using materials and processes with high mechanical strength. In the solid-state type, for example, a silicon nitride film is used as the membrane, and a nanometer-sized pore is provided in the membrane by irradiation of an electron beam or application of a voltage.

In the nanopore sequencer, it is important to dispose multiple nanopore sequencers in an array and measure the structure of biomolecules in parallel in order to improve a reading throughput. In arraying nanopore sequencers, not only the pores but also the peripheral structures such as associated liquid tanks and electrodes need to be parallelized.

For example, Patent Literature 1 discloses a method of arraying the solid-state type nanopore sequencers. The components of each sequencer are a membrane, a liquid tank, electrodes, and two flow paths for inflow and outflow, and the two flow paths are each configured by a mechanism which is connected to a valve and a pump through a pipe to supply a solution to each sequencer and recovers the solution.

CITATION LIST

Patent Literature

[Patent Literature 1] JP-A-2012-26986

SUMMARY OF INVENTION

Technical Problem

In arraying the solid-state type nanopore sequencers, in Patent Literature 1, two flow paths for inflow and outflow are provided in order to supply the solution to the liquid tank provided independently for each sequencer. In the structure having the flow path as described above, the array area is increased by an installation area of the flow path. This causes a factor that hinders integration and parallelization of sequencers. Furthermore, the provision of the pipe or the pump connected to the flow path to supply the solution increases a device area and the device cost.

Therefore, the present invention provides a method for forming a liquid tank capable of easily arraying solid-state type nanopore sequencers.

Solution to Problem

In the present invention, in arraying the solid-state type nanopore sequencers, the flow path is eliminated to improve the array integration degree, and the solution is introduced into the substrate to perform in-liquid bonding.

A method according to the present invention includes the steps of, as an example, introducing a solution between a substrate with a membrane in which the membrane is provided so as to close an opening and a substrate with an independent electrode in which the independent electrode is provided, pressure bonding the substrate with the membrane and the substrate with the independent electrode with a partition wall between the substrate with the membrane and the substrate with the independent electrode, and forming a sealed liquid tank surrounded by at least the membrane and the partition wall by the pressure bonding.

The method further includes the steps of, applying a voltage to the membrane to form a pore in the membrane, introducing a sample into the pore, and measuring a current flowing through the pore when the sample passes through the pore to analyze a structure of the sample, after forming the sealed liquid tank.

Also, as an example, a measurement device according to the present invention includes: a substrate with a membrane in which the membrane is provided so as to close an opening; a substrate with an independent electrode in which the independent electrode is provided; a partition wall that forms a compartment including the independent electrode between the substrate with the membrane and the substrate with the independent electrode; a first stage that is connected to the substrate with the membrane; a second stage that is connected to the substrate with the independent electrode; a mechanism that aligns the substrate with the membrane and the substrate with the independent electrode; a driver that brings the first stage and the second stage close to each other and presses the substrate with the membrane and the substrate with the independent electrode through the partition wall; a power supply for applying a voltage between an electrode disposed opposite to the independent electrode through the membrane and the independent electrode; and a measurement unit that measures a current flowing through the independent electrode by applying a voltage from the power supply.

Further, an analysis device according to the present invention includes: a substrate with a membrane in which a membrane is provided so as to close a plurality of openings disposed in an array; a substrate with independent electrodes in which a plurality of the independent electrodes are provided in an array; and a partition wall that forms a plurality of compartments each including each of the independent electrodes between the substrate with the membrane and the substrate with the independent electrodes, in which a plurality of liquid tanks filled with a solution are configured by the substrate with the membrane, the substrate with the independent electrodes and the partition wall, the plurality of the independent electrodes are substantially insulated by separation of the solution by the partition wall, and each of the liquid tanks has no flow path and the solution is sealed in each of the liquid tanks.

Advantageous Effects of Invention

According to the present invention, in arraying the solid-state type nanopore sequencers, no flow path is required, and independent liquid tanks can be arrayed with high degree of integration in each sequencer.

Further features of the present invention will be apparent from the description of the present specification and the accompanying drawings. Further, problems, configurations and effects other than those described above will be clarified by the description of the following embodiments.

DESCRIPTION OF EMBODIMENTS

Figure 1:
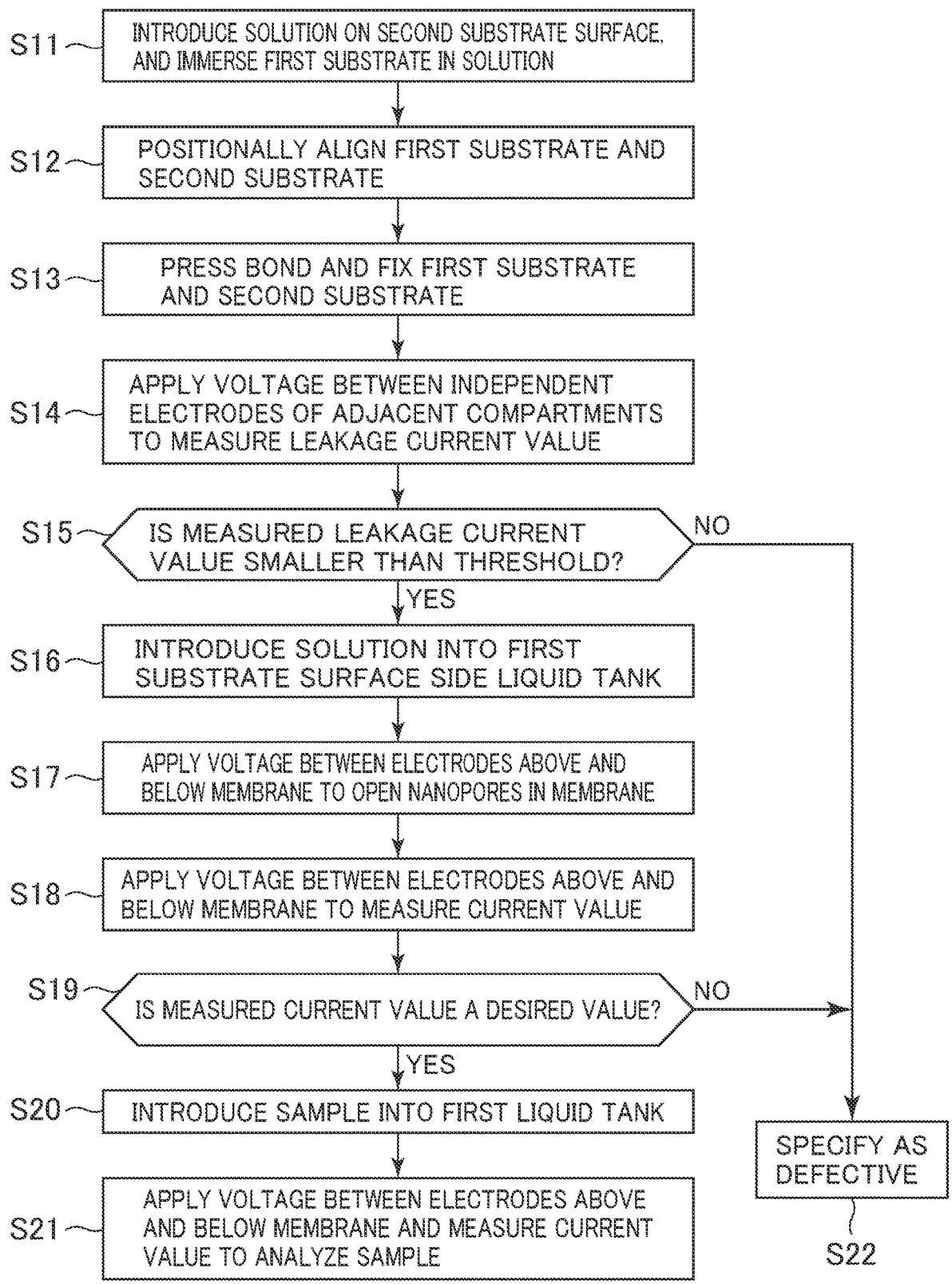
FIG. 1 is a flowchart showing an overall flow of an embodiment.

Hereinafter, embodiments of the present invention will be described with reference to the drawings. Each drawing is drawn schematically, and unnecessary parts for description will be omitted. The structures, materials, and formation methods described in the embodiments are merely examples for embodying the concept of the present invention, and do not strictly specify the materials, dimensions, and the like.

First Embodiment

First, an outline of an analysis device and a measurement device related to the present embodiment will be described.

FIGS. 5 to 10 are schematic cross-sectional views of main parts showing an example of the analysis device. The analysis device according to the present embodiment includes a substrate 113 with a membrane, a substrate 114 with independent electrodes, and a partition wall 106. The substrate 113 with the membrane has a membrane 100, a first substrate 101, a first electrode 102, and a first liquid tank support portion 103. The first substrate 101 is provided with a plurality of openings 120 penetrating through front and back surfaces of the first substrate 101 in an array. The membrane 100 is provided on one side of the first substrate 101 so as to close the plurality of openings 120 of the first substrate 101. The substrate 114 with the independent electrodes includes a second substrate 104 and independent electrodes 105A and 105B. The independent electrodes 105A and 105B are disposed in an array so as to correspond to the plurality of openings 120 of the first substrate 101 in a one-to-one manner. The first electrode 102 and the independent electrodes 105A and 105B are disposed opposite to each other through the membrane 100. The partition wall 106 have a plurality of openings corresponding to the independent electrodes disposed in the array, and the individual independent electrodes are surrounded one by one in each of the openings of the partition wall.

In this embodiment, for example, the membrane 100 is formed of a silicon nitride film, the first substrate 101 is formed of a silicon substrate, the first electrode 102 and the independent electrodes 105A and 105B are made of platinum, the second substrate 104 is formed of a glass epoxy substrate, and the partitions 106 are made of, for example, dimethyl polysiloxane. The second substrate 104 is provided with a wiring connected to the independent electrodes 105A and 105B and external output terminals. As an example, in this case, a size of a back surface opening of the first substrate is 250 µm$^2$, a diameter of the independent electrode of the second substrate is 150 µm, a diameter of the opening of the partition wall is 450 µm, and an array pitch is 700 µm.

Figure 2:
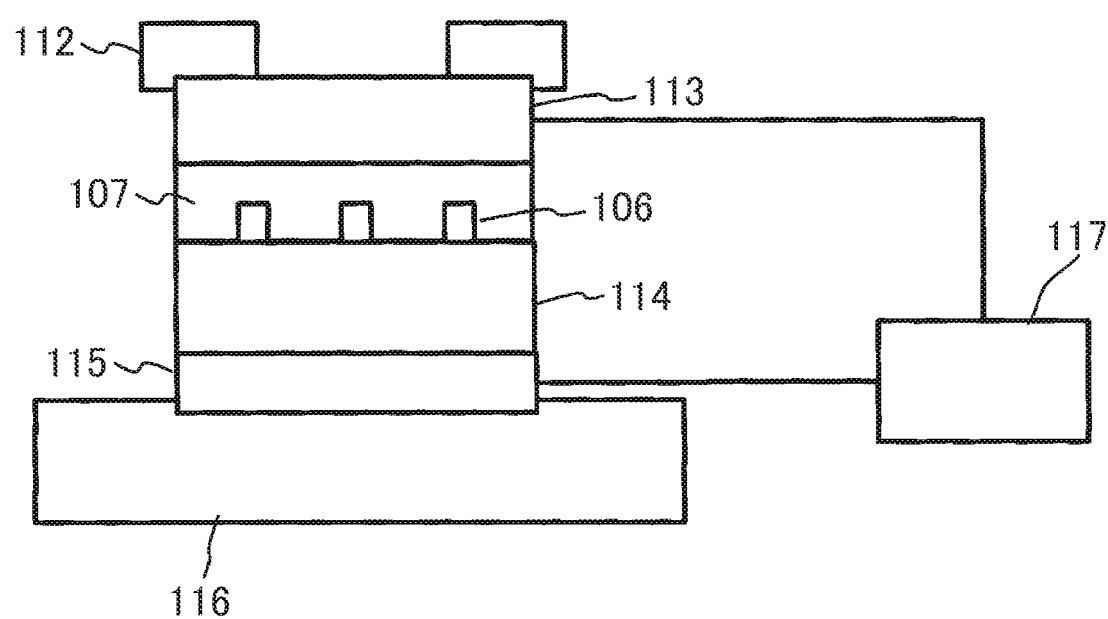
FIG. 2 is a schematic view of a main part showing one example of a measurement device.
Figure 3:
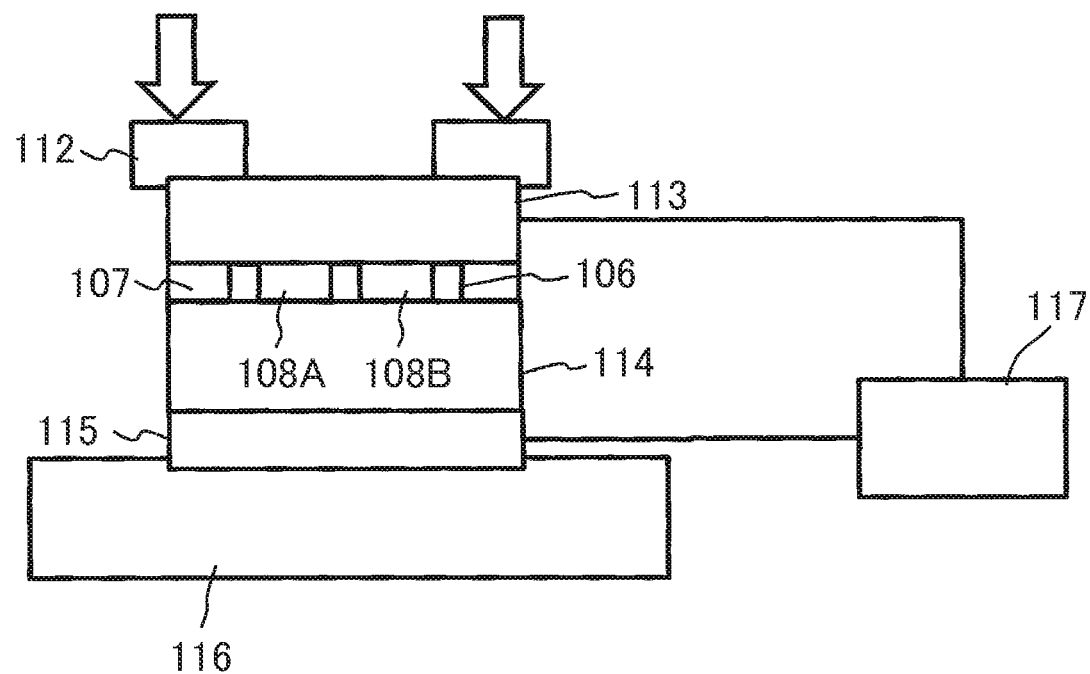
FIG. 3 is a schematic view of a main part showing another example of the measurement device.
Figure 4:
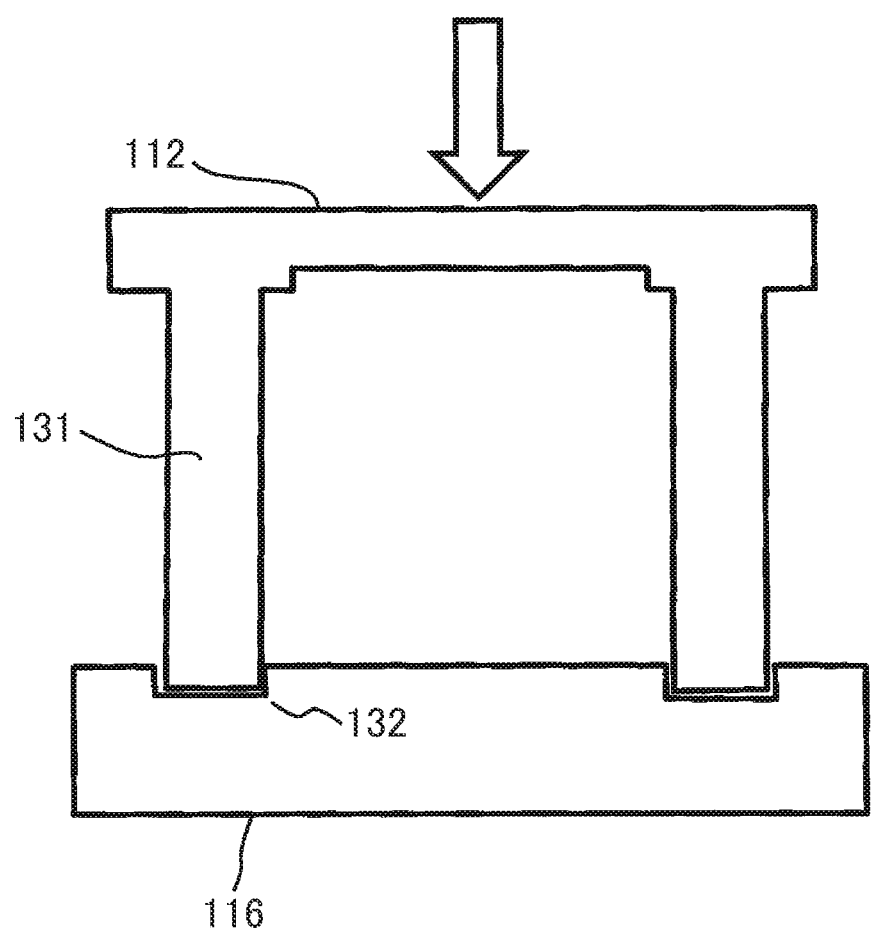
FIG. 4 is a schematic view showing one example of alignment.

FIGS. 2 and 3 are schematic diagrams of main parts of the measurement device according to the present embodiment. The measurement device according to the present embodiment has an upper stage 112, a lower stage 116, a control circuit unit 115, and a power supply and control/detection data acquisition unit 117. The upper stage 112 is opened in a region for introducing a solution or a sample, and is operated to press the substrate 113 with the membrane of the analysis device against the substrate 114 with the independent electrodes. In addition, as shown in FIG. 4, the upper stage 112 is provided with insertion pins 131, and the lower stage 116 is provided with recesses 132 corresponding to the insertion pins 131 for introducing the pins. The insertion pins 131 and the recesses 132 serve as guides for aligning when pressing the substrate. The control circuit unit 115 is wired to the independent electrodes 105A and 105B, the power supply and control/detection data acquisition unit 117, controls a voltage to be applied to the independent electrodes, and transfers a signal obtained during measurement to a PC. The power supply and control/detection data acquisition unit 117 includes at least a high output power supply, a processor such as a CPU (central processing unit), a memory, and a storage unit such as a hard disk.

FIG. 1 is a flowchart showing the overall flow up to a pore formation and sample analysis step including a liquid tank formation step of the analysis device according to the present embodiment. Although the details of a laminated chip in a case where a number of arrays is two will be described below, it is needless to say the number of arrays may be one or more than two.

(1) Step S11

Figure 5:
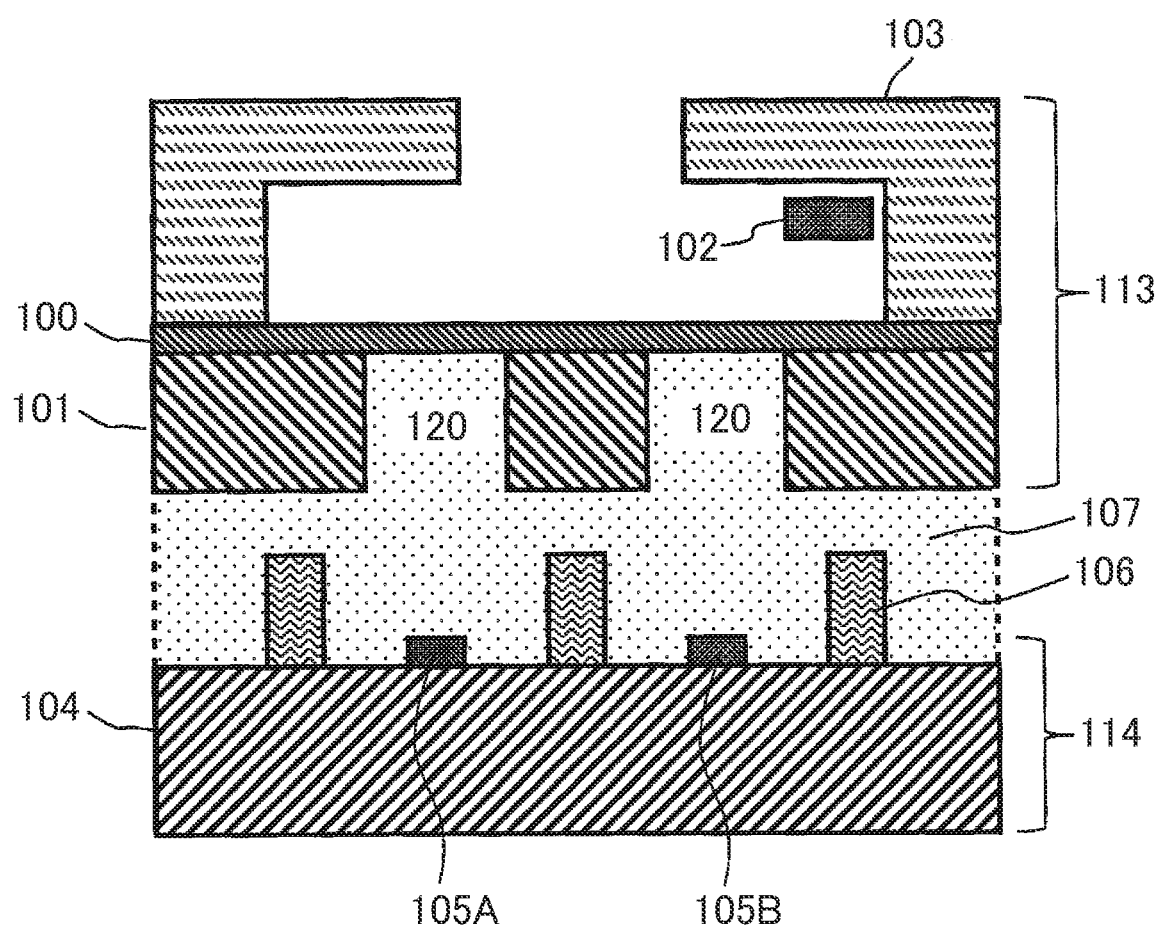
FIG. 5 is a schematic sectional view of a main part showing one example of an analysis device.

First, as shown in FIG. 2, the substrate 114 with the independent electrodes having the partition wall 106 is attached to the control circuit unit 115 and the lower stage 116, and in a state where the substrate 113 with the membrane is attached to the upper stage 112, a solution 107 is introduced on the substrate 114 with the independent electrodes to immerse one surface of the substrate 113 with the membrane in the solution 107. Thus, the solution is introduced between the substrate 113 with the membrane and the substrate 114 with the independent electrodes. The introduction of the solution 107 is performed so as to cover the plurality of openings of the partition wall 106. As shown in FIG. 5, through the solution introduction process, a space between the membrane 100 and the independent electrodes 105A and 105B is filled with the solution. The solution 107 contains an electrolyte such as KCl.

(2) Step S12

Next, the upper stage 112 is driven to the lower stage 116 side, and as shown in FIG. 4, the insertion pins 131 and the recesses 132, which are provided on the upper stage 112 and the lower stage 116, respectively, are combined to mechanically align positions of the upper stage 112 and the lower stage 116. With the above alignment step, the substrate 113 with the membrane and the substrate 114 with the independent electrodes are aligned such that the openings 120 of the first substrate 101 and the independent electrodes of the substrate 114 with the independent electrodes correspond to each other in a one-to-one manner.

The substrate with the membrane 113 is precisely attached to the upper stage by being fitted into a recess provided in the upper stage 112. In addition, the substrate 114 with the independent electrodes is precisely attached to the lower stage 116 by being fitted into a recess provided in the lower stage 116 together with the control circuit unit 115. Therefore, according to the present embodiment, the upper stage 112 and the lower stage 116 are aligned, thereby performing the alignment of the substrate 113 with the membrane and the substrate 114 with the independent electrodes. The order of the process of Step S11 and the process of Step S12 may be reversed.

(3) Step S13

Further, as shown in FIG. 3, the upper stage 112 is brought closer to the lower stage 116, and the substrate 113 with the membrane and the substrate 114 with the independent electrodes are pressure bonded through the partition wall 106 to fix the positions of the substrate 113 with the membrane and the substrate 114 with the independent electrodes.

Figure 6:
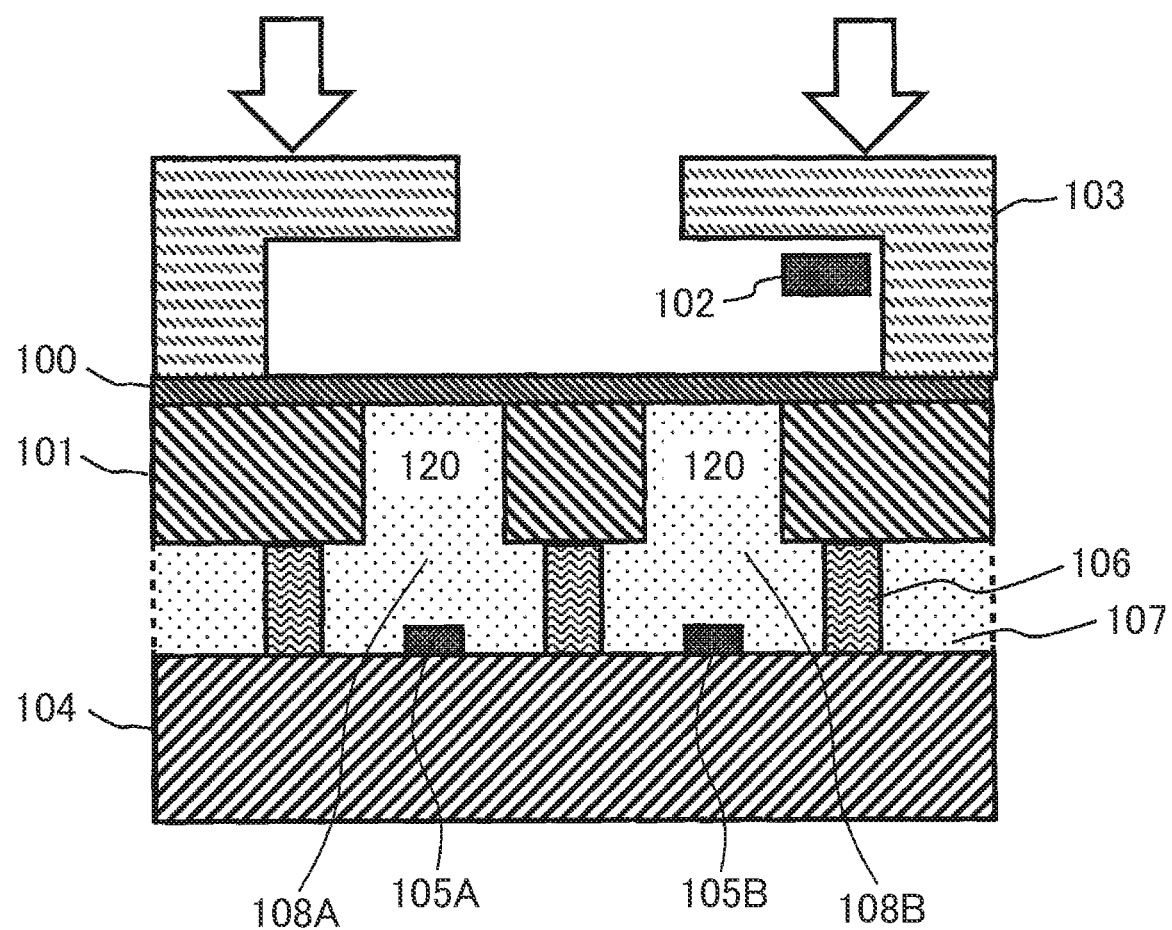
FIG. 6 is a schematic sectional view of a main part showing another example of the analysis device.

As shown in FIG. 6, after the alignment and pressure bonding steps, the plurality of partitions in which the membrane 100 is exposed from the openings 120 of the first substrate 101 and the independent electrodes 105A and 105B are aligned so as to correspond to each other. Thus, a plurality of independent liquid tanks 108A and 108B separated by the partition wall 106 are formed. In other words, the sealed independent liquid tanks surrounded by the membrane 100 and the partitions 106 can be formed without using a flow path. The plurality of independent electrodes 105A and 105B are substantially insulated by separation of the solution by the partition wall 106, and there is no flow path in the liquid tanks, and the solution is sealed in the liquid tanks.

(4) Step S14

In this embodiment, if there is a solution leak between the independent liquid tanks 108A and 108B, various problems occur such as pores will not be formed in a pore forming step to be described later, and signal noise will occur in a sample analysis step. Therefore, a voltage is applied between the adjacent independent electrodes 105A and 105B, and a leak current value is measured.

(5) Step S15

For the leak current value, a certain level that does not have a problem in the pore formation step and the sample analysis step to be described later is set as a threshold, and the measured leak current value is compared with the threshold. The threshold value is set to, for example, 100 pA, which is sufficiently smaller than a current flowing through the pores in Step S21 to be described later, when the applied voltage is 0.1 V.

If it is determined in Step S15 that the leak current value is equal to or greater than the threshold value, the process proceeds to Step S22, and the partition having the independent liquid tanks 108A and 108B in which the leak current is detected is identified as defective. The defective partition or the non-defective partition is stored in a storage unit.

(6) Step S16

Figure 7:
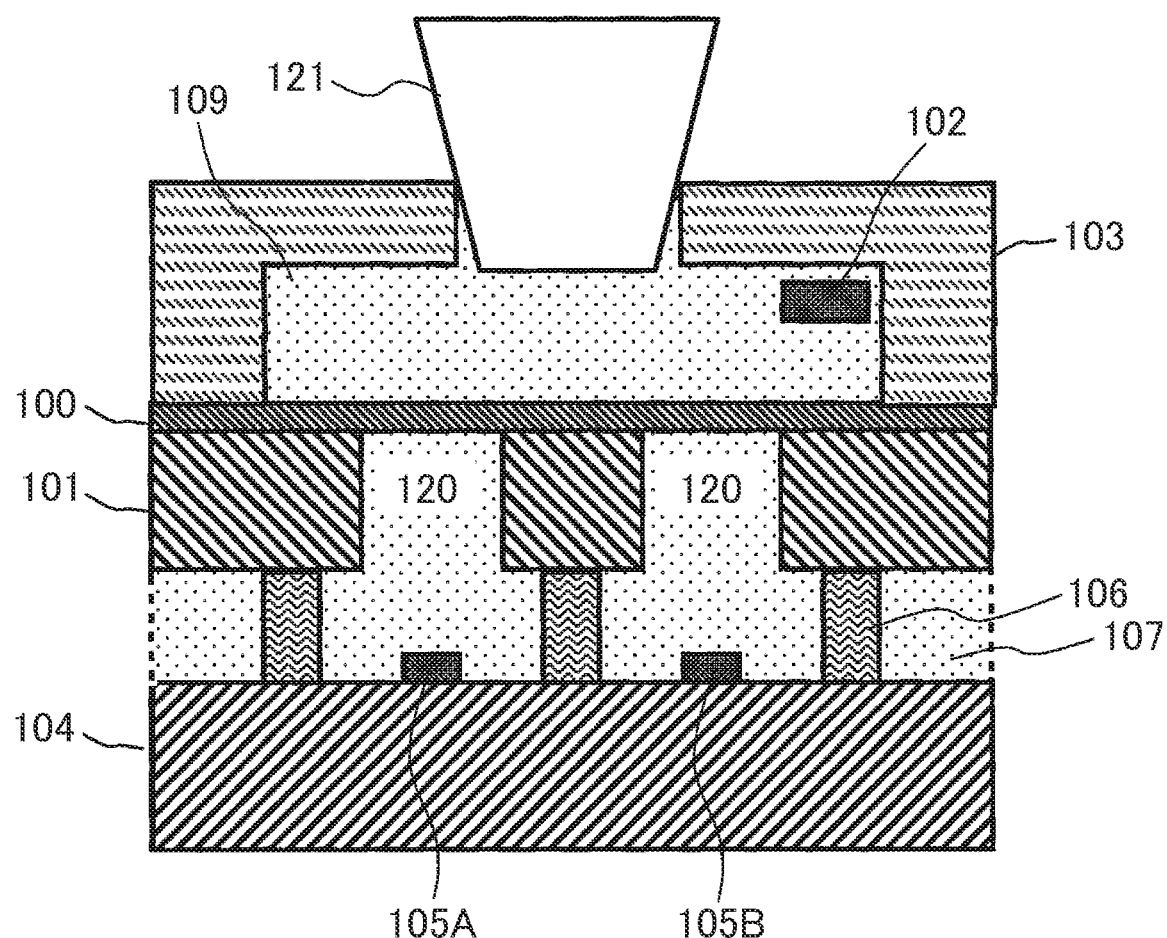
FIG. 7 is a schematic sectional view of a main part showing another example of the analysis device.

If it is determined in Step S15 that the leak current value is smaller than the threshold value, the process proceeds to Step S16, and as shown in FIG. 7, a solution is introduced to an upper side of the membrane 100 with the use of a nozzle 121 containing the solution to the first liquid tank 109. As a result, the upper side and a lower side of the membrane 100 are filled with the solution.

(7) Step S17

Figure 8:
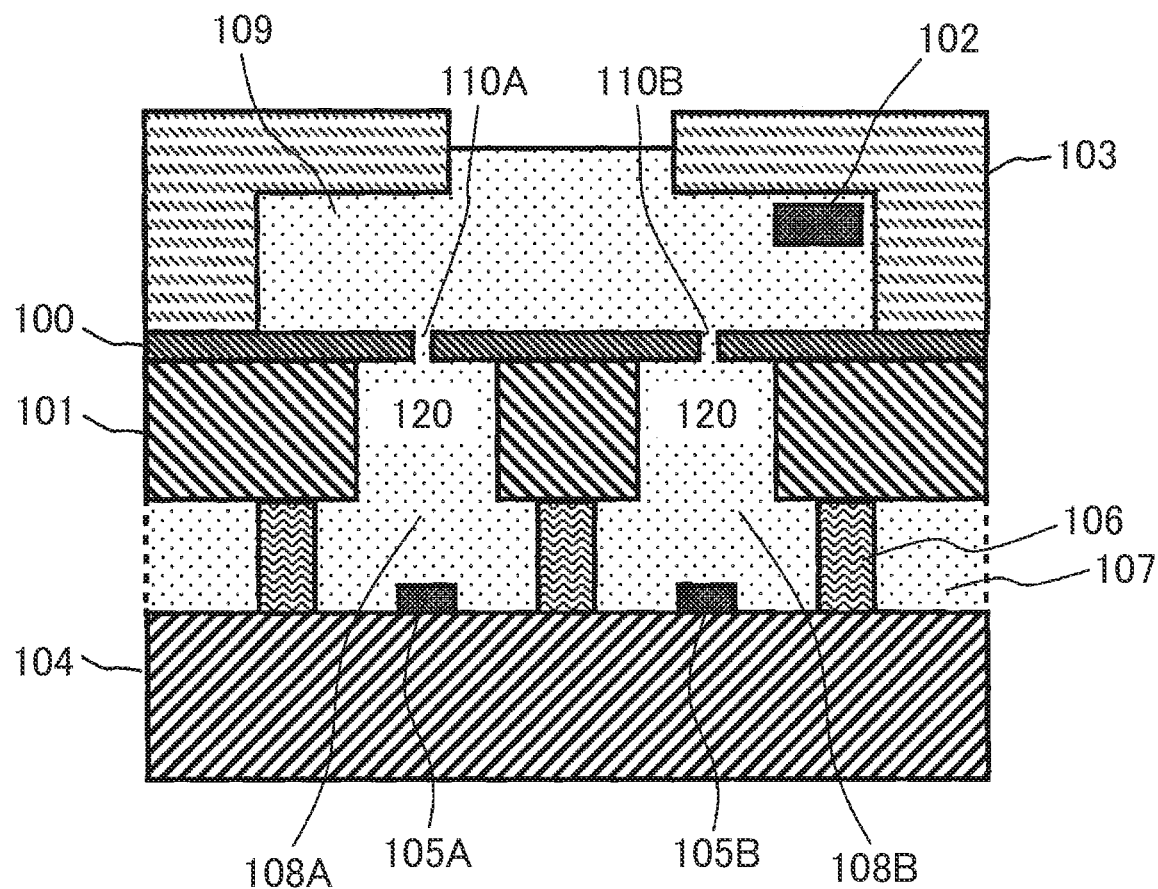
FIG. 8 is a schematic sectional view of a main part showing another example of the analysis device.

Subsequently, as shown in FIG. 8, a voltage is applied between the first electrode 102 and each of the independent electrodes 105A and 105B, and pores 110A and 110B of a nanometer size are formed in the membrane 100 by a known mechanism of dielectric breakdown.

(8) Step S18

In this embodiment, since the diameters of the pores 110A and 110B becomes larger as the value of the current flowing through the pores becomes larger, the diameters can be controlled by the value of the current (refer to WO 2015/097765 A). However, when the membrane 100 is not sufficiently hydrophilized and the membrane 100 does not contact the solution, a voltage is not normally applied to the upper and lower sides of the membrane, and no pores are formed. For that reason, a voltage smaller than the voltage applied in the pore forming step is applied between the first electrode and the plurality of independent electrodes 105A and 105B in order to determine whether the pores of a desired size have been formed. The value of the current flowing between the first electrode 102 and the plurality of independent electrodes 105A and 105B is measured.

(9) Step S19

It is determined whether the value of the current flowing between the first electrode 102 and each of the independent electrodes 105A and 105B is a value corresponding to the pores of the desired size.

If there is a partition in which the value of the current flowing between the first electrode 102 and the independent electrodes 105A and 105B does not reach a certain current amount, the partition is determined to be defective. Thereafter, the process proceeds to Step S22, and the defective partition is stored in the storage unit.

The control circuit unit 115 controls the voltage applied to each of the independent electrodes and the sequence, and performs the pore formation in parallel in a plurality of partitions. There is no need to carry out the step of applying the voltage or the step of measuring the current in the partition determined to be defective after the formation of the liquid tank described above. If the pore formation step and the current value measurement step described above are performed only in the non-defective partition, the pore formation can be performed efficiently.

(10) Step S20

Figure 9:
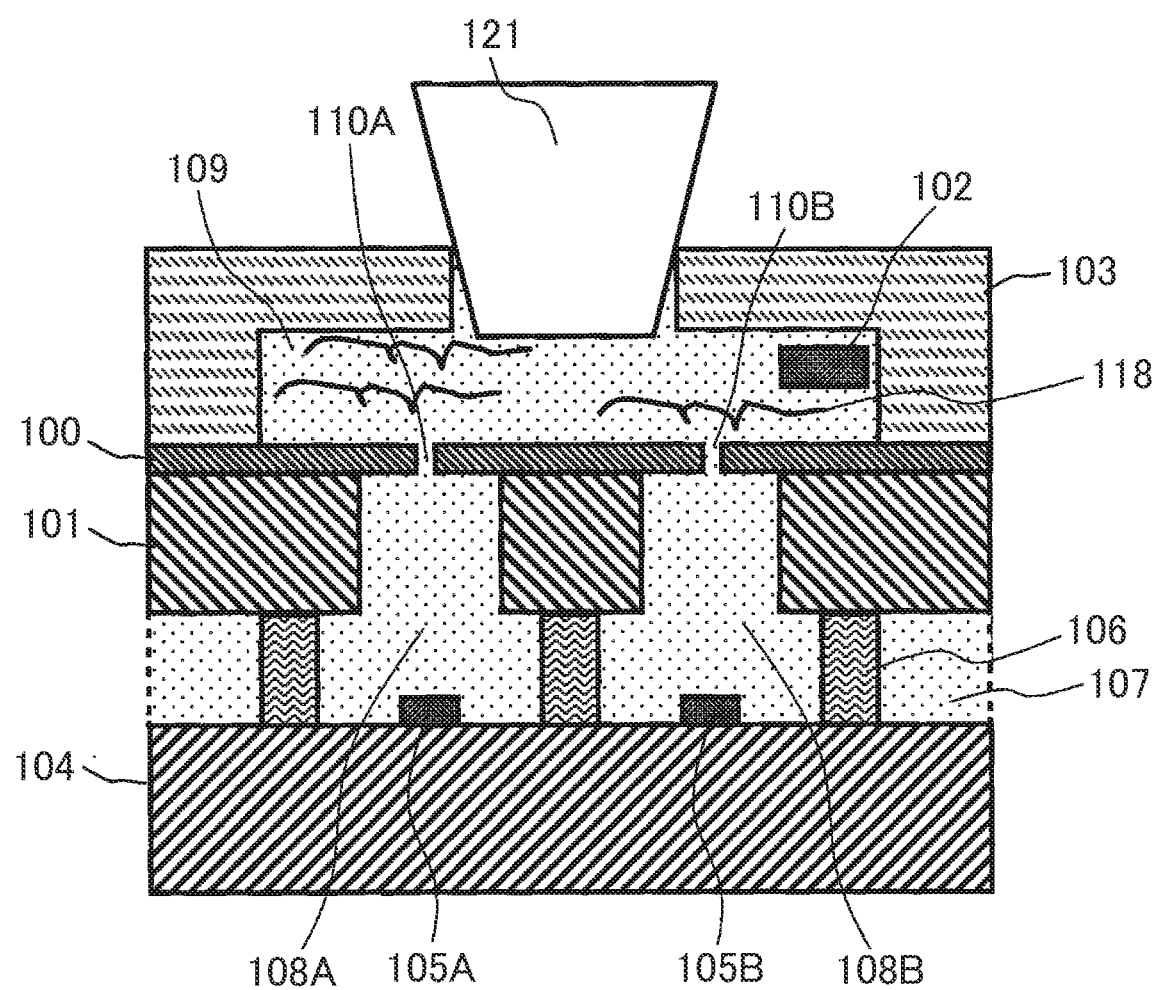
FIG. 9 is a schematic sectional view of a main part showing another example of the analysis device.

Next, as shown in FIG. 9, a sample 118 is introduced from the nozzle 121 into the first liquid tank 109.

(11) Step S21

Figure 10:
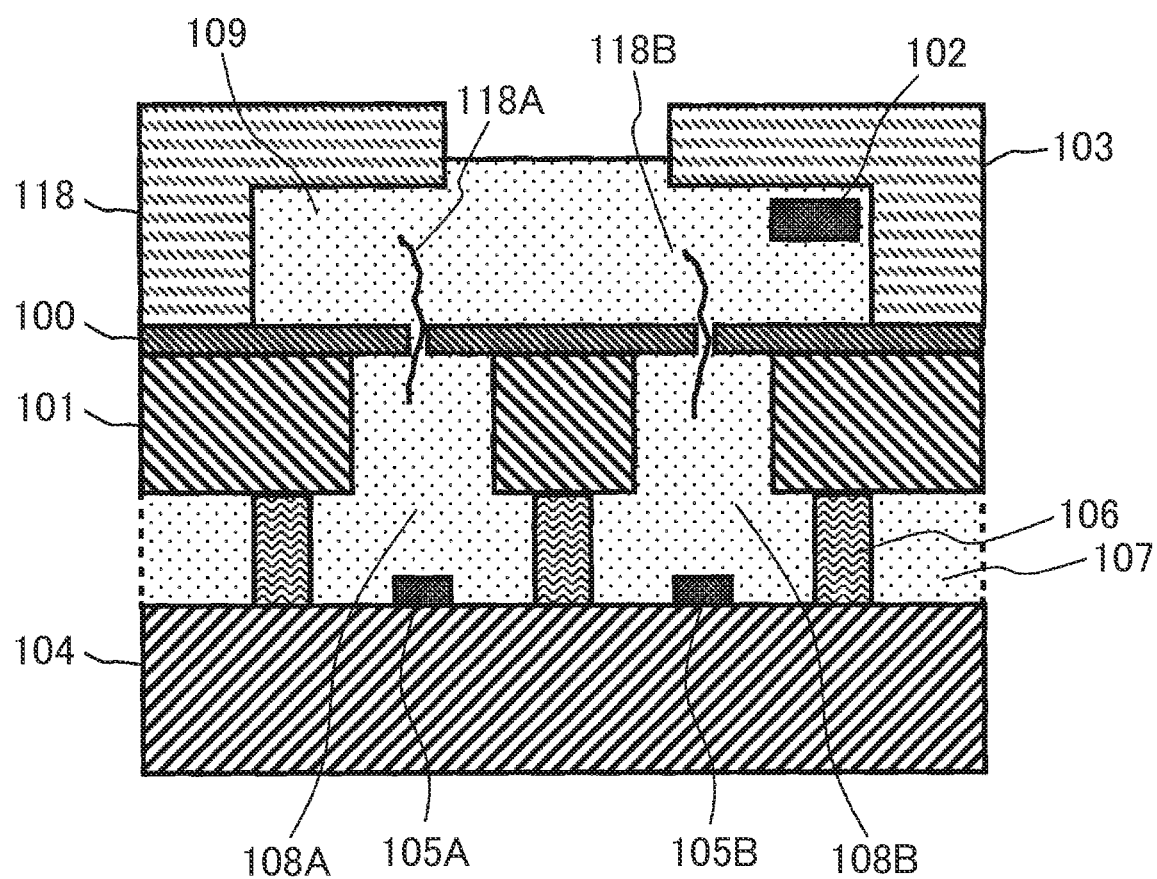
FIG. 10 is a schematic sectional view of a main part showing another example of the analysis device.

Finally, as shown in FIG. 10, a voltage is applied between the first electrode 102 and the independent electrodes 105A and 105B. With the application of a voltage, an electric field is generated around the pores 110A and 110B, and an electrophoretic force is generated so that biological samples 118A and 118B charged in the liquid are attracted to the electric field. As a result, the samples 118A and 118B are introduced into the pores 110A and 110B and pass through the pores 110A and 110B. In this embodiment, the detected current value changes between before the biological samples pass through the pores 110A and 110B and while the biological samples 118A and 118B pass through the pores 110A and 110B. This is because the pores 110A and 110B are partially blocked and resistance values of the pores 110A and 110B changes depending on cross-sectional areas of the biological samples 118A and 118B. The structure of the sample is analyzed from those measured current values. The structural analysis of the sample by the blockage current measurement may be performed on a partition other than the defective partition.

Through the steps described above, a plurality of independent liquid tanks sealed without any flow path are realized, and the pore formation and the sample analysis are realized with the use of the plurality of independent liquid tanks.

Figure 11:
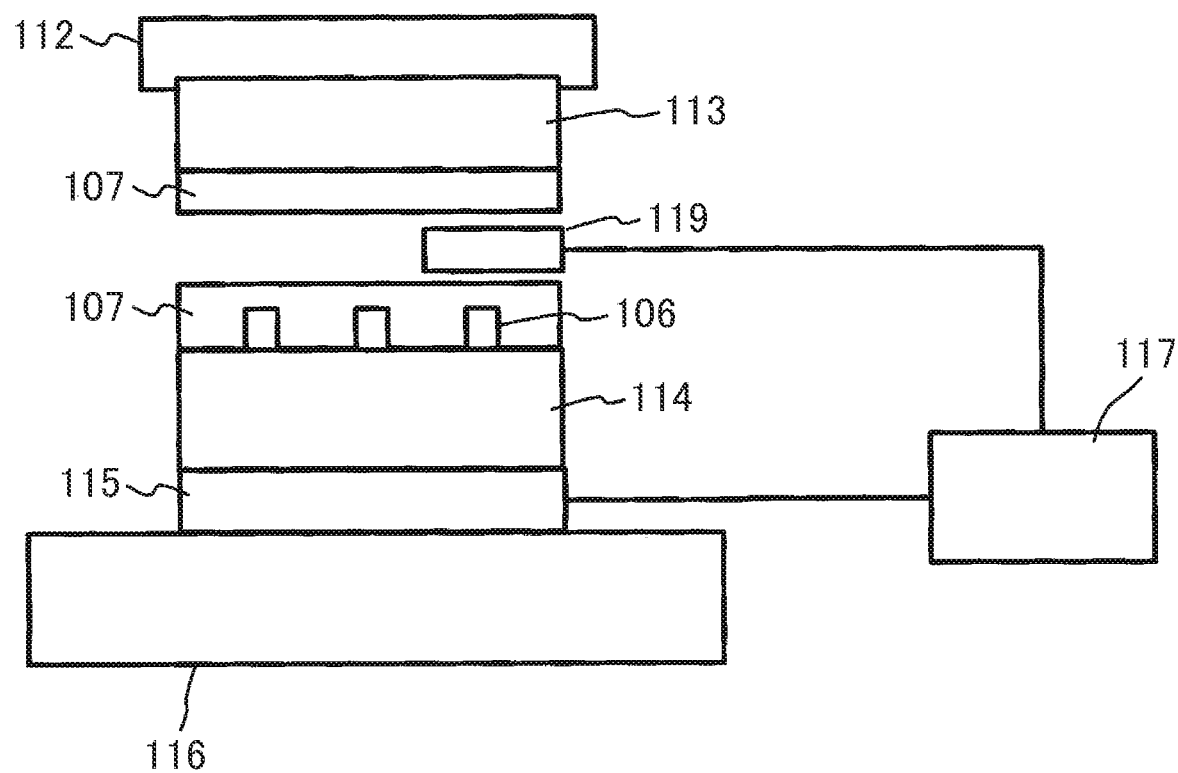
FIG. 11 is a schematic view showing another example of alignment.

Incidentally, the contents described in the embodiment described above are merely examples, and the present invention is not limited to the above configuration. The mechanical alignment method of aligning the insertion pin is used for position alignment between the substrate with the membrane and the substrate with the independent electrodes. However, for example, as shown in FIG. 11, a camera 119 may be mounted on the device, and a positional relationship between a pattern provided on the substrate 113 with the membrane and a pattern provided on the substrate 114 with the independent electrodes may be recognized, and the relative positions of those substrates may be controlled. Also, the arrangement of an optical system represented by the camera is not limited to between the substrates. The driving of the upper stage 112 and the lower stage 116 may be performed with the use of an existing type such as a lever type, a motor or pneumatic control, or the like.

Although the control circuit unit 115 is an independent part, the control circuit unit 115 may be provided on the second substrate 104 or may be disposed in the power supply and the control/detection data acquisition unit 117, and variations of the device are various. A system suitable for the measurement environment may be configured.

Also in the analysis device, for example, the silicon nitride film is used for the membrane, but a silicon oxide film, graphene, graphite, an organic substance, or a polymer material may be used. Platinum is used for the electrodes, but other metals such as silver-silver chloride, gold and the like may be used. The first substrate is placed so that the membrane is on the upper side, but the first substrate may be located on the upper side of the membrane. Although the second substrate is formed of the glass epoxy substrate, another printed substrate such as Teflon (registered trademark), a glass substrate, or a silicon substrate may be used.

Figure 12:
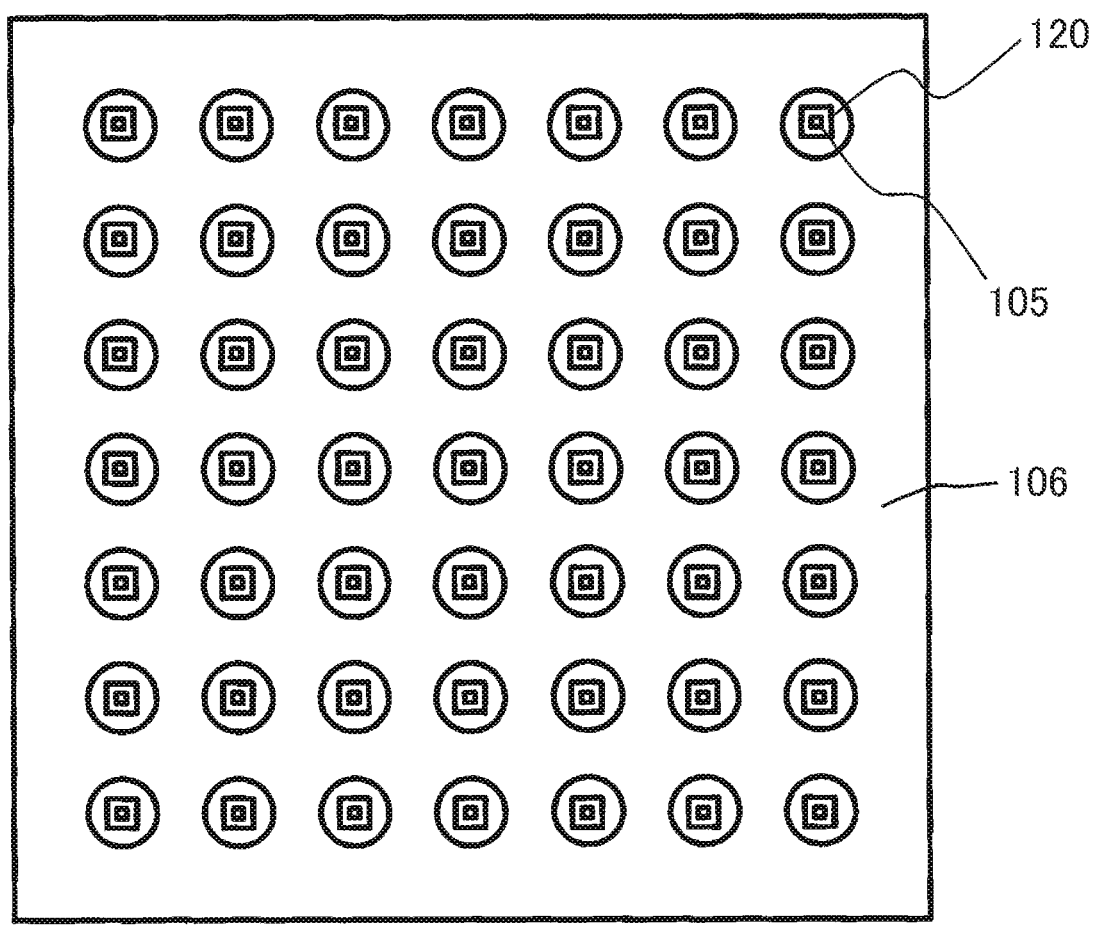
FIG. 12 is a conceptual plan view illustrating a layout of a first substrate, a partition wall, and a second substrate.

FIG. 12 is a schematic plan view illustrating a layout of the first substrate 101, the partition wall 106, and the second substrate 104 when the number of arrays is 49 (seven rows, seven columns). The partition 106 shown in FIG. 12 has circular openings corresponding to the independent liquid tanks 108A and 108B in FIG. 6, and the other area is a layout in which the partition material is disposed in a solid film. In other words, the space between adjacent independent liquid tanks is filled with the partition wall. Further, the opening 120 of the first substrate shown by a square is the opening provided in the first substrate 101 in FIG. 5, and a back surface of the membrane 100 is exposed. As shown in FIG. 12, the opening 120 of the first substrate and the independent electrode 105 are contained in the independent liquid tank divided by the opening of the partition wall 106.

In the present embodiment, as shown in FIG. 5, the partition wall 106 is provided on the second substrate 104 side, but may be provided on the first substrate 101 side. Although the partition wall is made of dimethylpolysiloxane, the material of the partition wall is not limited to the above material as long as the material is an insulator and a material such as an elastomer which can sufficiently adhere between the first substrate and the second substrate by the pressure bonding.

Although the first liquid tank support portion 103 has a configuration in which the first liquid tank 109 has a ceiling, the present invention is not limited to the above configuration. For example, the first liquid tank support may have a wall shape surrounding four sides of a bank, and a large opening may be provided in the upper part of the first liquid tank, and other configurations may be applied. Furthermore, in a case of a configuration in which the large opening is provided in the upper part of the first liquid tank, a measure for introducing the sample into the pores is not limited to electrophoresis, and a drive mechanism for controlling the position of the sample may be placed on a membrane top, and the drive mechanism may be used to control a movement of the sample (refer to WO 2016/088486 A).

The pores 110A and 110B may be formed in the membrane 100 in advance. In the present embodiment, the pores 110A and 110B are formed by applying a voltage to the membrane 100, but the present invention is not limited to the above configuration. The pores 110A and 110B may be formed by other methods such as irradiating the membrane 100 with an electron beam (refer to A J Storm et al., Nat. Mat. 2 (2003)).

Furthermore, at the time of solution introduction, it is necessary that the wettability between the analysis device and the solution be high. In order to enhance the wettability, it is effective to subject the substrate 113 with the membrane and the substrate 114 with the independent electrodes to a surface treatment prior to solution introduction. As the surface treatment to improve the wettability, the analytical device may be immersed in a mixture of hydrogen sulfide and hydrogen peroxide to remove organic matters, or an alcohol may be introduced before the solution is introduced, and the alcohol may be replaced with the solution. Alternatively, the analytical device may be oxygen plasma treated. Moreover, those treatments may be combined together.

Second Embodiment

In the present embodiment, another example of a method of introducing a solution which can obtain the same effect as that of the first embodiment will be described. Since the method of the first embodiment is applied except the introduction method of the solution, a description of the process and the structure will be omitted. The difference from the process of the first embodiment described with reference to FIG. 1 is only a process of a first step S11, and therefore only the process of Step S11 in the present embodiment will be described, and a description of the subsequent processes will be omitted.

Figure 13:
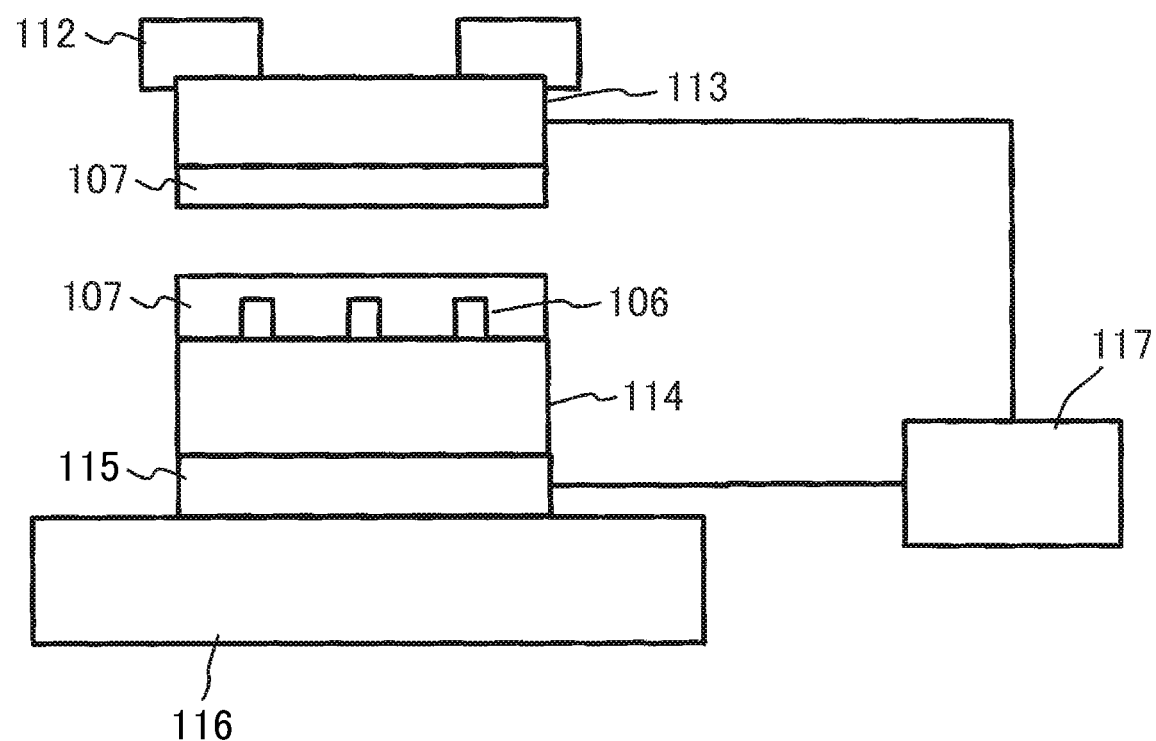
FIG. 13 is a schematic view of a main part showing one example of a measurement device.

FIG. 13 is a schematic view of a main part of a measurement device according to the present embodiment. In the present embodiment, as shown in FIG. 13, the introduction of a solution 107 in the formation of the independent liquid tanks in FIG. 1 is performed in two places on one surface of a substrate 113 with a membrane and one surface of a substrate 114 with independent electrodes. For example, in order to introduce the solution into the substrate 113 with the membrane, an upper stage 112 is used to invert a back surface so that the back surface is located on an upper side, and the solution 107 is introduced to the back surface of the substrate 113 with the membrane in an inverted state. However, if the solution introducing portion of the substrate 113 with the membrane is in a state of sufficiently high wettability, the solution can be introduced without inverting the substrate. The method for introducing the solution into the substrate 114 with the independent electrodes is omitted because the method conforms to the contents described in the first embodiment.

Next, the upper stage 112 and the lower stage 116 are brought closer to each other to bring the solutions introduced into the two substrates into contact with each other. Thereafter, position alignment is performed, and the substrate with the membrane and the substrate with the electrodes are pressure bonded to each other through the partition wall 106. As shown in FIG. 3, through the solution introduction, alignment and pressure bonding steps, a plurality of independent liquid tanks 108A and 108B separated from each other by the partition wall 106 are formed. In other words, the sealed independent liquid tanks can be formed without using a flow path.

Third Embodiment

The present embodiment shows a device structure which reduces a defective rate at the time of formation of a liquid tank as compared with the analysis device shown in the first embodiment.

In the first embodiment, when the partition wall and the substrate in an area located outside the analysis device are pressure bonded to each other before the partition wall and the substrate in an area located inside the analysis device is pressure bonded to each other, due to a flatness of the analysis device, or the like, the solution stays between the partition wall and the substrate in an area located inside the device. If the solution remains between the partition wall and the substrate as it is, the solution leaks between the independent liquid tanks, and the partition in which the stay occurs becomes defective. Further, if the solution is further pressed to eliminate the leak of the solution, the staying solution may flow into the independent solution tank, as a result of which the pressure in the independent solution tank may be increased, and the membrane may be damaged.

Figure 14:
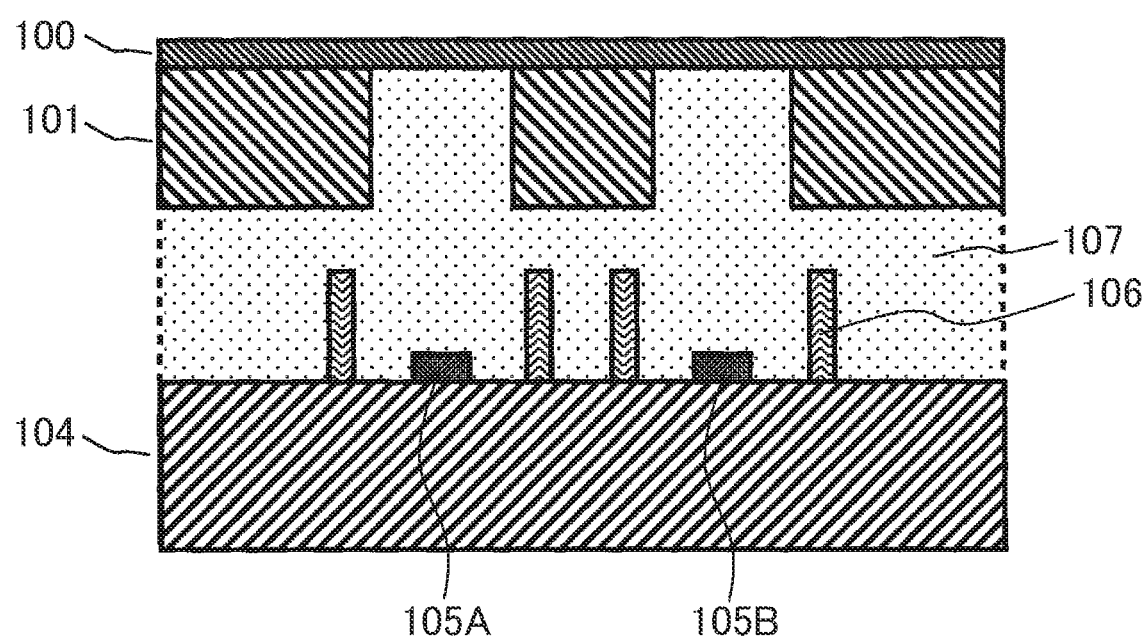
FIG. 14 is a schematic sectional view of a main part showing one example of an analysis device.
Figure 15:
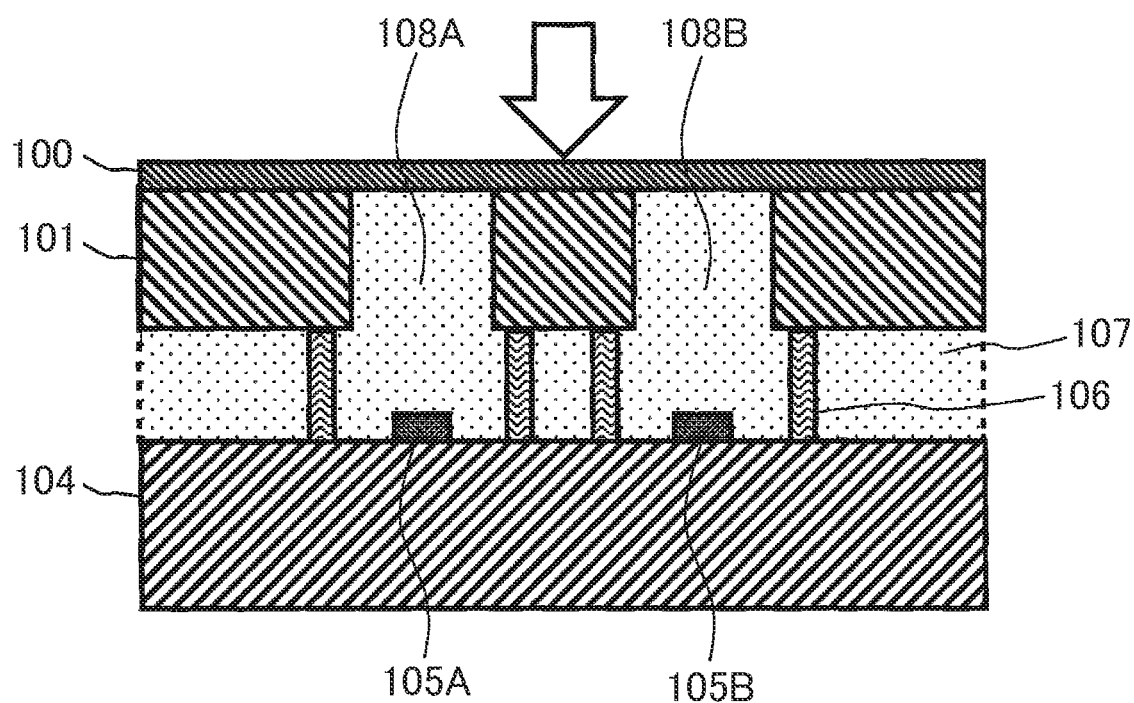
FIG. 15 is a schematic sectional view of a main part showing another example of the analysis device.
Figure 16:
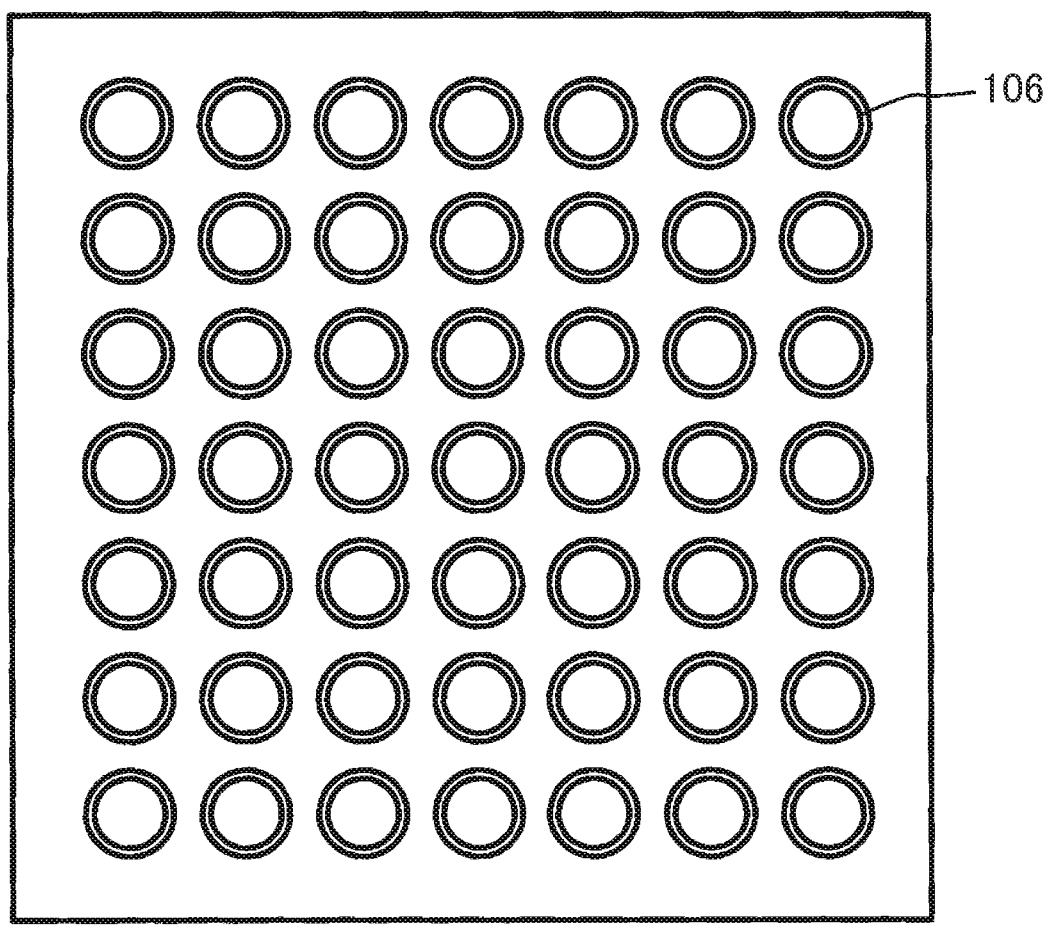
FIG. 16 is a diagram showing a planar layout of a partition wall.

According to the present embodiment, since the structure and method of the first embodiment are applied except for the partition walls, a description of the process and the structure will be omitted. FIGS. 14 and 15 are cross-sectional schematic views of a main part of an analysis device according to the present embodiment. FIG. 16 is a diagram showing a planar layout of the partition walls in the present embodiment when the number of arrays is 49 (seven rows, seven columns). As shown in FIG. 16, each of partition walls 106 is shaped in a ring, an inside of the ring is an area of an independent liquid tank, and an outside of the ring is an area that communicates with the outside of the device. As shown in the cross-sectional schematic views of FIGS. 14 and 15, the partition walls are present in a double manner between the adjacent independent electrodes 105A and 105B.

FIG. 14 is a schematic cross-sectional view of a main part of the device after the solution introduction and position alignment steps. A space between a membrane 100 and the independent electrodes 105A and 105B is filled with a solution 107, and the solution also intervenes between the partition walls 106 and a first substrate 101.

FIG. 15 is a schematic cross-sectional view of a main part of the analysis device after the pressure bonding step. As shown in FIG. 15, after the pressure bonding step, independent liquid tanks 108A and 108B are formed by the ring-shaped partition walls 106. In this embodiment, even when the partition 106 and the first substrate 101 in the area located outside the analysis device are pressure bonded before the partition 106 and the first substrate 101 in the region located inside the analysis device are pressure bonded, a sealed state can be formed between the independent tanks 108A and 108B by the partition walls 106. In the case of the structure of the present embodiment, the ring outer side of the partition 106 is connected to the outer side of the analysis device, and there is an area lower pressure than the solution area in the adjacent part of the liquid tank, that is, there is a space opened between the partition walls. For that reason, an excess solution is discharged to the outside from a space between the partition walls 106 and a failure due to the stay of the solution can be prevented. In addition, since the excess solution does not flow into the independent liquid tanks 108A and 108B, damage to the membrane 100 can also be prevented.

In this embodiment, a formation method of the ring-shaped partition walls is mentioned, for example: if a photosensitive resin is used for partition material, the ring-shaped partition walls can be formed with the use of a lithography method. Alternatively, the ring-shaped partition walls can be formed by a method of pressing a mold using a soft lithography method or a method of arranging O-rings. However, the formation method is not limited to those methods.

Further, the ring-shaped partition walls are not limited to circular shapes, and may be polygonal or irregular as long as the partition walls can form the independent liquid tanks.

Fourth Embodiment

The present embodiment shows a device structure which improves the reliability of the device compared with the analysis device shown in the third embodiment. Since the structure and method of the third embodiment are applied except for the partition walls, a description of the process and the structure will be omitted.

Figure 17:
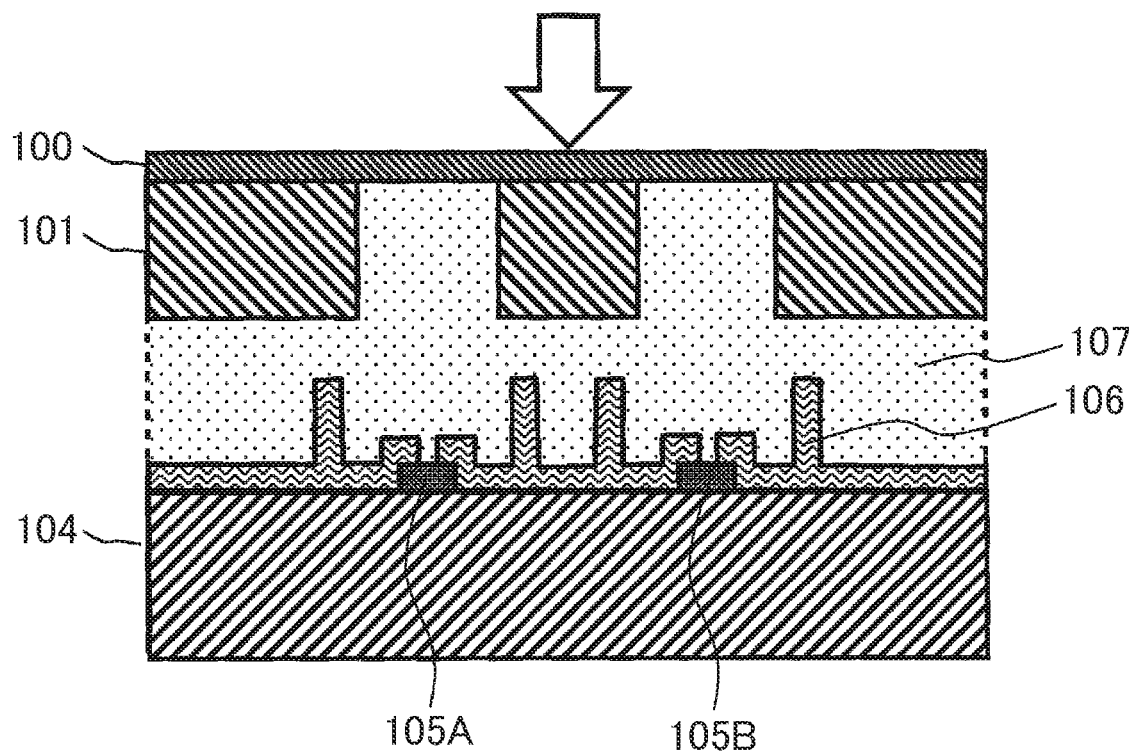
FIG. 17 is a schematic sectional view of a main part showing another example of the analysis device.
Figure 18:
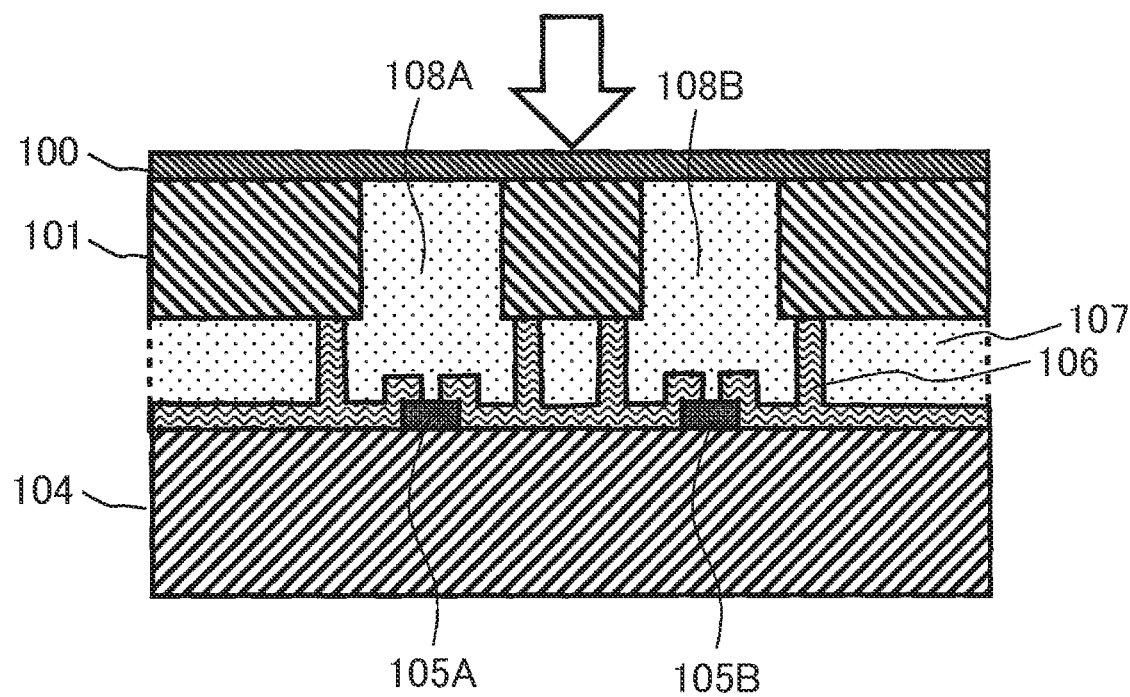
FIG. 18 is a schematic sectional view of a main part showing another example of the analysis device.

FIGS. 17 and 18 are cross-sectional schematic views of a main part of an analysis device according to the present embodiment. Each of partition walls 106 in the present embodiment has a structure in which a surface of a second substrate 104 is covered except for a partial region of independent electrodes 105A and 105B. FIG. 17 is a schematic cross-sectional view of a main part of the device after the solution introduction and position alignment steps. A space between the two substrates 101 and 104 is filled with a solution 107. FIG. 18 is a schematic cross-sectional view of the main part of the analysis device after the pressure bonding step. As shown in FIG. 18, after the pressure bonding process, independent liquid tanks 108A and 108B are formed by the partition walls 106.

In this embodiment, the highest surface of the partition walls 106 have the same ring-like structure as that in the third embodiment, and the ring outer side of the partition walls are connected to the outside of the analysis device, that is, spaces between the partition walls are released. For that reason, an excess solution is discharged from between the partition walls and a failure due to the stay of the solution can be prevented. Furthermore, when the components of the solution change properties such as swelling or dissolution of a material of the second substrate, the structure of the partition walls in the present embodiment is a structure in which the second substrate 104 and the solution 107 do not come in direct contact with each other. For that reason, the second substrate 104 can be protected from the solution.

In this embodiment, the method for forming the ring-shaped partition walls 106 is mentioned, for example: after a material of the partition wall is applied to the second substrate 104, the partition walls 106 can be formed by a method of pressing a mold with the use of a soft lithography method. If it is difficult to form a penetration pattern by pressing the mold, openings can be provided by irradiating portions where the independent electrodes 105A and 105B are exposed with a laser beam after pressing by the mold. Alternatively, the ring-shaped partition walls can be formed by a method in which an isotropic etching in plasma is performed and openings are provided so that at least a part of the independent electrode is exposed, instead of the laser. However, the method of forming the ring-shaped partition walls 106 is not limited to those methods.

Fifth Embodiment

The present embodiment shows a device structure for reducing a defective rate at the time of forming a liquid tank, as compared with the analysis device shown in the first embodiment. In the first embodiment, when an excess solution flows into the independent liquid tank, the membrane may be damaged to cause a failure.

Figure 19:
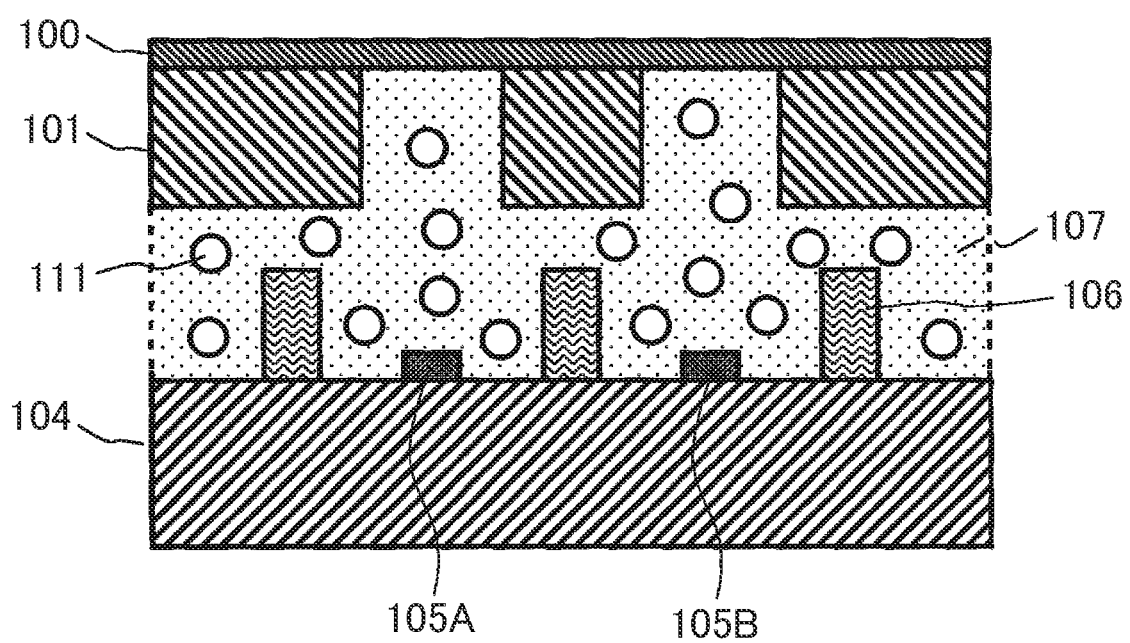
FIG. 19 is a schematic sectional view of a main part showing another example of the analysis device.
Figure 20:
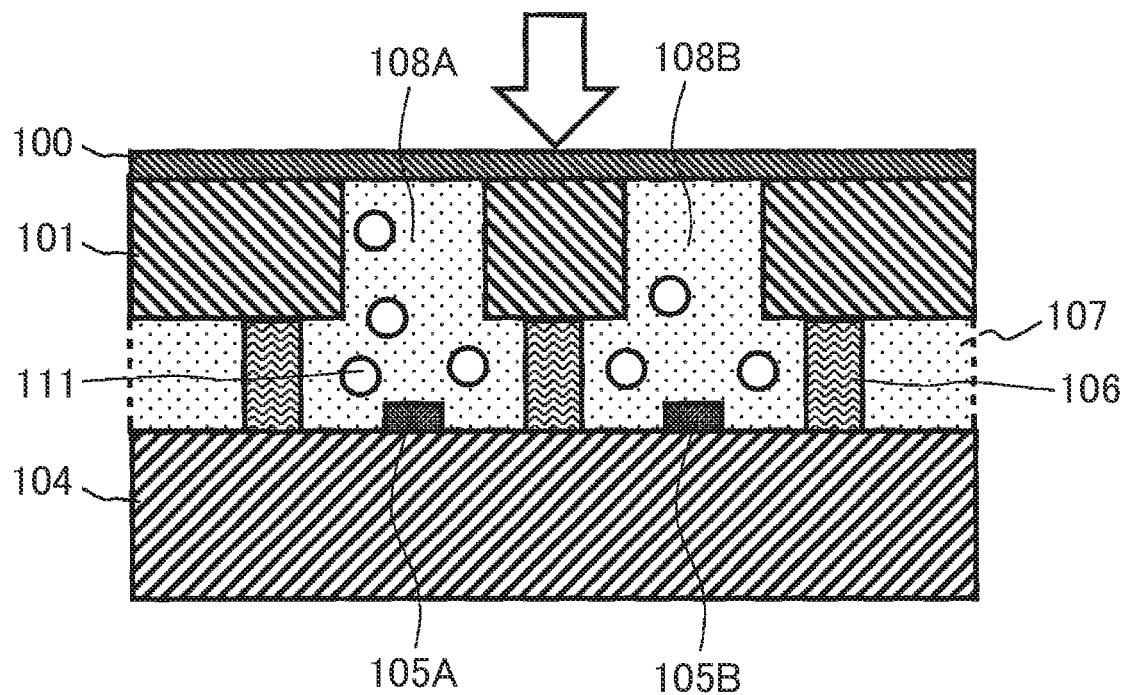
FIG. 20 is a schematic sectional view of a main part showing another example of the analysis device.

In the present embodiment, the same structure as that in the first embodiment is applied except for the structure in the liquid tank. FIGS. 19 and 20 are cross-sectional schematic views of a main part of the analysis device according to the present invention. FIG. 19 is a schematic cross-sectional view of a main part of the device before the position alignment step after solution introduction. A space between the two substrates is filled with a solution 107. In this embodiment, in the solution 107, a plurality of gas phase regions 111 are provided.

FIG. 20 is a schematic cross-sectional view of a main part of the analysis device after the pressure bonding step. As shown in FIG. 20, after the pressure bonding step, independent liquid tanks 108A and 108B are formed by partition wall 106. In this embodiment, even when an excess solution flows into the independent liquid tank, a sealed state can be formed between the independent liquid tanks 108A and 108B by the partition wall 106. In the present embodiment, since the gas phase region 111 is provided in the independent liquid tank as a region having a lower pressure than the solution region, the volume of the gas phase region 111 is contracted by the pressure in the liquid tank even if the pressure in the liquid tank is increased by the solution inflow. As a result, the pressure rise in the liquid tank can be prevented, and the membrane damage can be prevented.

In this embodiment, a method of forming the gas phase region 111 is mentioned, for example: microbubbles are generated in the solution with the use of an ejector method, a cavitation method, a swirl flow method, a pressure dissolution method, etc., and a solution having microbubbles is introduced by a method introduced by the method described in the first embodiment or the second embodiment. Alternatively, the gas phase region can also be formed using thermally expandable microcapsules. However, the method of forming the gas phase region is not limited to those methods.

According to the first to fifth embodiments described above, the degree of integration of devices can be improved by eliminating the flow path in the formation of a solid-state type nanopore sequencer array. In addition, the method of supplying the solution to the independent liquid tank can be simplified.

The present invention is not limited to the embodiments described above, but includes various modifications. The above embodiments have been described in detail in order to describe the present invention in an easy-to-understand manner, and are not necessarily limited to those having all the described configurations. Also, a part of a configuration of one embodiment can be replaced with the configuration of another embodiment. Also, the configuration of another embodiment can be added to the configuration of one embodiment. In addition, with respect to a part of the configuration of each embodiment, another configuration can be added, deleted, or replaced.

LIST OF REFERENCE SIGNS

100: membrane
101: first substrate
102: first electrode
103: first liquid tank support
104: second substrate
105, 105A, 105B: independent electrodes
106: partition wall
107: solution
108A, 108B: independent liquid tank
109: first liquid tank
110A, 110B: pore
111: gas phase region
112: upper stage
113: substrate with membrane
114: substrate with independent electrodes
115: control circuit unit
116: lower stage
117: power supply and control/detection data acquisition unit
118, 118A, 118B: sample
119: camera
120: opening of first substrate
121: nozzle

The invention claimed is:
1. A method comprising the steps of:
introducing a solution between a substrate with a membrane in which the membrane is provided to close a plurality of openings disposed in an array and a substrate with independent electrodes in which a plurality of the independent electrodes are disposed in an array;

aligning the substrate with the membrane and the substrate with the independent electrodes to cause the openings to correspond to the independent electrodes in a one-to-one manner;
pressure bonding the substrate with the membrane and the substrate with the independent electrodes with a partition wall between the substrate with the membrane and the substrate with the independent electrodes, the partition wall having a plurality of openings corresponding to the independent electrodes disposed in the array; and
forming a sealed liquid tank surrounded by at least the membrane and the partition wall by the pressure bonding,
wherein in the step of introducing the solution, the solution is introduced to cover the plurality of openings of the partition wall to form a plurality of sealed liquid tanks surrounded by at least the membrane and the partition wall having the plurality of openings, and
wherein the method further comprises the steps of:
applying a voltage between the adjacent independent electrodes to measure a leak current after forming the plurality of sealed liquid tanks; and
determining that a compartment including the independent electrodes to be defective when a value of the leak current is equal to or more than a preset threshold.

2. A method comprising the steps of:
introducing a solution between a substrate with a membrane in which the membrane is provided to close a plurality of openings disposed in an array and a substrate with independent electrodes in which a plurality of the independent electrodes are disposed in an array;
aligning the substrate with the membrane and the substrate with the independent electrodes to cause the openings to correspond to the independent electrodes in a one-to-one manner;
pressure bonding the substrate with the membrane and the substrate with the independent electrodes with a partition wall between the substrate with the membrane and the substrate with the independent electrodes, the partition wall having a plurality of openings corresponding to the independent electrodes disposed in the array; and
forming a sealed liquid tank surrounded by at least the membrane and the partition wall by the pressure bonding,
wherein in the step of introducing the solution, the solution is introduced to cover the plurality of openings of the partition wall to form a plurality of sealed liquid tanks surrounded by at least the membrane and the partition wall having the plurality of openings, and
wherein the method further comprises the steps of:
after forming the plurality of sealed liquid tanks,
applying a voltage to the membrane to provide a pore in the membrane;
measuring a current flowing through the pore, and setting a compartment in which the current does not reach a certain current value as a defective compartment;
introducing a sample into the pores; and
measuring a current flowing through the pore in a compartment other than the defective compartment when the sample passes through the pore to analyze a structure of the sample.

* * * * *